(12) United States Patent
Chen et al.

(10) Patent No.: US 12,077,787 B2
(45) Date of Patent: Sep. 3, 2024

(54) DIACYLGLYCEROL ACYLTRANSFERASE 1 AND APPLICATION THEREOF IN PRODUCTION OF TRIACYLGLYCEROL

(71) Applicants: Haiqin Chen, Wuxi (CN); Wei Chen, Wuxi (CN); Xin Tang, Wuxi (CN); Jun Cao, Wuxi (CN); Jianxin Zhao, Wuxi (CN); Yongquan Chen, Wuxi (CN); Hao Zhang, Wuxi (CN)

(72) Inventors: Haiqin Chen, Wuxi (CN); Wei Chen, Wuxi (CN); Xin Tang, Wuxi (CN); Jun Cao, Wuxi (CN); Jianxin Zhao, Wuxi (CN); Yongquan Chen, Wuxi (CN); Hao Zhang, Wuxi (CN)

(73) Assignee: Jiangnan University, Wuxi (CN)

( * ) Notice: Subject to any disclaimer, the term of this patent is extended or adjusted under 35 U.S.C. 154(b) by 499 days.

(21) Appl. No.: 17/469,899

(22) Filed: Sep. 9, 2021

(65) Prior Publication Data
US 2021/0403884 A1 Dec. 30, 2021

Related U.S. Application Data

(63) Continuation of application No. PCT/CN2019/083866, filed on Apr. 23, 2019.

(30) Foreign Application Priority Data

Mar. 21, 2019 (CN) .......................... 201910216803.3

(51) Int. Cl.
*C12N 9/10* (2006.01)
*C12P 7/6445* (2022.01)

(52) U.S. Cl.
CPC .......... *C12N 9/1029* (2013.01); *C12P 7/6445* (2013.01); *C12Y 203/0102* (2013.01)

(58) Field of Classification Search
CPC .. C12Y 203/0102; C12N 1/185; C12N 15/63; C12P 7/6463
See application file for complete search history.

(56) References Cited

FOREIGN PATENT DOCUMENTS

CN 101437953 5/2009

OTHER PUBLICATIONS

Luo et al. Biotechnol. Lett., 2017, 39, 883-888 (Year: 2017).*
Cao J. et al. Identification and functional characterization of diacylglycerol acyltransferase 1 from Mortierella alpina. Science Paper Online. Jun. 2, 2019. p. 1-12.

* cited by examiner

*Primary Examiner* — Lianko G Garyu
*Assistant Examiner* — Lioubov G Korotchkina
(74) *Attorney, Agent, or Firm* — Lili Chen

(57) ABSTRACT

Disclosed is a diacylglycerol acyltransferase 1, a recombinant *Saccharomyces cerevisiae* containing the diacylglycerol acyltransferase 1, and application thereof in production of triacylglycerol. The diacylglycerol acyltransferase 1 of the invention has a function of catalyzing synthesis of triacylglycerol. After the recombinant *Saccharomyces cerevisiae* containing the diacylglycerol acyltransferase 1 of the invention is subjected to induction culture for 48 h, the content of total fatty acid and triacylglycerol in the recombinant *Saccharomyces cerevisiae* containing the diacylglycerol acyltransferase 1 can be respectively increased by 1.94 folds and 12.09 folds as compared with those of *Saccharomyces cerevisiae* without the recombinant diacylglycerol acyltransferase 1. The instant invention provides a method for improving the ability of microorganisms to produce polyunsaturated fatty acids (PUFAs) by means of genetic engineering.

7 Claims, 13 Drawing Sheets
Specification includes a Sequence Listing.

DIACYLGLYCEROL ACYLTRANSFERASE 1 AND APPLICATION THEREOF IN PRODUCTION OF TRIACYLGLYCEROL

CROSS-REFERENCE TO RELATED APPLICATIONS

This application is a continuation of international application PCT/CN2019/083866, filed Apr. 23, 2019, which claims the benefit of priority to Chinese patent application No. 2019102168033, filed Mar. 21, 2019, the content of which are hereby incorporated by reference in the entirety.

BACKGROUND OF THE INVENTION

Field of the Invention

The invention relates to a diacylglycerol acyltransferase 1 and its application in production of triacylglycerol, belonging to the technical field of enzyme engineering and microbial engineering.

Description of the Related Art

Polyunsaturated fatty acids (PUFAs) are straight-chain fatty acids that contain two or more double bonds and have a carbon chain length of 18-22 carbon atoms. The polyunsaturated fatty acids have a function of reducing cardiovascular and cerebrovascular diseases and play a very important role in maintaining good health and preventing diseases. Therefore, the polyunsaturated fatty acids have a huge market at home and abroad as a health-care product.

At present, most of the polyunsaturated fatty acids (PUFAs) sold in the market are obtained from aquatic phytoplankton, and the viscera of deep-sea fish such as wild cod, herring and salmon that feed on such plants are also rich in polyunsaturated fatty acids (PUFAs). However, because the long growth cycle and high cultivation cost of such animals and plants and the fact that polyunsaturated fatty acids (PUFAs) derived from these animals and plants can no longer meet the growing market demands, it is urgent to find other ways to increase the production of polyunsaturated fatty acids (PUFAs).

Studies have shown that some microorganisms such as bacteria and fungi also have the function of producing lipids, and these microorganisms such as bacteria and fungi have many advantages such as short growth cycle, fast reproduction rate, low production cost, environmental friendliness, and are unconstrained by geographical environment and climatic conditions. In addition, these microorganisms such as bacteria and fungi also have the benefits of high oil yield and diverse oil composition. Therefore, it is a promising way to increase the production of polyunsaturated fatty acids (PUFAs) by producing oils with microorganisms.

Lipids produced from microorganisms include glycerides, lipoids (phospholipids, sterols and the like) and free fatty acids, among which triacylglycerol (TAG) is the most important storage form of microbial lipids. Triacylglycerol (TAG) in microorganisms is mainly synthesized through the Kennedy pathway on the endoplasmic reticulum. Acyl coenzyme A:diacylglycerol acyltransferase (DGAT, EC 2.3.1.20) is the key rate-limiting enzyme in the Kennedy pathway that can catalyze the process of adding a fatty acid acyl to the position sn-3 of diacylglycerol.

At present, the reported DGATs are divided into four types: DGAT1, DGAT2, DGAT3 and DGAT/WS. Among them, DGAT1 and DGAT2 are ubiquitous in eukaryotes. Although they have low homology and are two different enzymes, they both play an important role in TAG synthesis in organisms. For example, Bouvier-Navé P, et al. expressed the *Arabidopsis* dgat gene in yeast, which increased the DGAT activity in recombinant yeast by 200-600 times and the TAG accumulation by 3-9 times. Besides, although they have wide fatty acid substrate preferences, they will also give preference to specific fatty acid substrates in some cases. For example, Taylor D C, et al. found that the DGAT1 of *Brassica napus* prefers palmitic acid, and Shockey, J. M, et al. found that the DGAT2 of tung tree prefers α-eleostearic acid. In view of the important regulatory role of DGAT in the fatty acid synthesis process, it is of great significance to further study DGAT's function for directionally enhancing lipid accumulation of oleaginous microorganisms, and thus increasing the production of polyunsaturated fatty acids (PUFAs) of oleaginous microorganisms.

However, not all DGATs can promote lipid accumulation of oleaginous microorganisms. For example, in the article "Identification and functional analysis of acyl-CoA:diacylglycerol acyltransferase from oleaginous fungus *Mucor circinelloides*", dgat1 genes in *Mucor circinelloides* were heterologously expressed in *Saccharomyces cerevisiae* through a vector pYES2. The results showed that the two DGAT1 enzymes did not show the ability to synthesize TAG (Reference: Zhang Luning, Identification and functional analysis of acyl-CoA:diacylglycerol acyltransferase from oleaginous fungus *Mucor circinelloides*, Jiangnan University, 2015). In the article "Cloning and Functional Characterization of Diacylglycerol Acyltransferase Gene (MtDGAT1) from *Medicago truncatula*", dgat1 gene of *Medicago truncatula* was heterologously expressed in *Saccharomyces cerevisiae*. It was found that the MtDGAT1-1 did not show the ability to synthesize TAG (Reference: Xu Ronghua, Cui Tao, Wang Jiancai, Cloning and Functional Characterization of Diacylglycerol Acyltransferase Gene (MtDGAT1) from *Medicago truncatula*, Acta Botanica Boreali-Occidentalia Sinica, 2016, 36(10):1941-1947). In the article "Identification and characterization of diacylglycerol acyltransferase from oleaginous yeast *Rhodosporidium toruloides*", dgat1 in *Rhodosporidium toruloides* was heterologously expressed in *Saccharomyces cerevisiae* through a vector pYES2. The results showed that the DGAT1 enzyme did not show the ability to synthesize TAG (Reference: Wang Zhen, Identification and characterization of diacylglycerol acyltransferase from oleaginous yeast *Rhodosporidium toruloides*, Jiangnan University, 2016). Therefore, it is particularly important to choose an appropriate DGAT.

*Mortierella alpina* (*M. alpina*) is an oleaginous filamentous fungus with strong lipid synthesis ability, and its total fatty acid content can reach 50% or more of the dry cell weight. The content of ω-6 polyunsaturated fatty acid: arachidonic acid (ARA) accounts for 30%-40% of the total lipids. Therefore, *Mortierella alpina* (*M. alpina*) is a very high-quality ARA-producing fungus, and DGAT from *M. alpina* has relatively high potential to promote lipid accumulation of oleaginous microorganisms. However, there were a few reports on DGAT in *M. alpina*, and the only reports were focused on DGAT2. For example, Jeennor S and Luo X A, et al. found that DGAT2 in *M. alpina* can increase the content of TAG and have a specific fatty acid preference. So far, there is no relevant research report on DGAT1 in *M. alpina*.

If DGAT1 from *M. alpina* can be obtained successfully, by performing bioinformatics analysis and expressing it in model microorganisms to study the function of the enzyme, a more substantial theoretical basis for further increasing the production of TAG and specific PUFAs in microorganisms can be achieved.

SUMMARY OF THE INVENTION

The present invention provides a recombinant *Saccharomyces cerevisiae* expressing diacylglycerol acyltransferase 1, wherein the recombinant *Saccharomyces cerevisiae* carrying a recombinant vector pYES2-Madgat1b, wherein the recombinant vector pYES2-Madgat1b is constructed by connecting a gene encoding the diacylglycerol acyltransferase 1 to vector pYES2, wherein the nucleotide sequence of the diacylglycerol acyltransferase 1 gene is as set forth in SEQ ID NO: 2. The amino acid sequence of the diacylglycerol acyltransferase 1 is as set forth in SEQ ID NO: 1.

In an embodiment of the invention, the *Saccharomyces cerevisiae* is *Saccharomyces cerevisiae* INVSc1.

In an embodiment of the invention, it provides a preparation method of the diacylglycerol acyltransferase 1, using the recombinant *Saccharomyces cerevisiae*, including: adding the recombinant *Saccharomyces cerevisiae* to a culture medium without uracil for culture of 36-48 hr, collecting cells, adding the collected cells to an induction culture medium without glucose but with galactose and obtain an initial $OD_{600}$ of 0.3-0.5, and continuing induction culture for 48-96 h to obtain the diacylglycerol acyltransferase 1.

In an embodiment of the invention, the culture medium includes an SC-U culture medium.

In an embodiment of the invention, the culture is carried out at a temperature of 28-30° C. at a rotation speed of 200-250 rpm.

In an embodiment of the invention, it provides a method for producing triacylglycerol, using the recombinant *Saccharomyces cerevisiae*, including: adding the recombinant *Saccharomyces cerevisiae* to a culture medium without uracil for culture for 36-48 h, collecting cells, adding the collected cells to an induction culture medium without glucose but with galactose and obtain an initial $OD_{600}$ of 0.3-0.5, continuing induction culture for 48-96 h to obtain triacylglycerol.

In an embodiment of the invention above, the culture medium includes an SC-U culture medium.

In an embodiment of the invention above, the culture is carried out at a temperature of 28-30° C. at a rotation speed of 200-250 rpm.

The diacylglycerol acyltransferase 1 of the invention has the function of catalyzing synthesis of triacylglycerol (TAG). After the recombinant *Saccharomyces cerevisiae* containing the diacylglycerol acyltransferase 1 of the invention is subjected to induction culture for 48 h, the total fatty acid content and the triacylglycerol content in the recombinant *Saccharomyces cerevisiae* containing the diacylglycerol acyltransferase 1 of the invention can be respectively increased by 1.94 and 12.09 folds as compared to the *Saccharomyces cerevisiae* without the diacylglycerol acyltransferase 1, and contents of monounsaturated fatty acids 16:1 and 18:1 in the triacylglycerol can be respectively increased by 10.36 and 9.14 folds as compared with the *Saccharomyces cerevisiae* without the diacylglycerol acyltransferase 1. The invention provides a method for improving PUFA production in recombinant microorganisms and pave the road for large scale production of PUFAs in industrial microorganisms.

DETAILED DESCRIPTION

Figure 1:
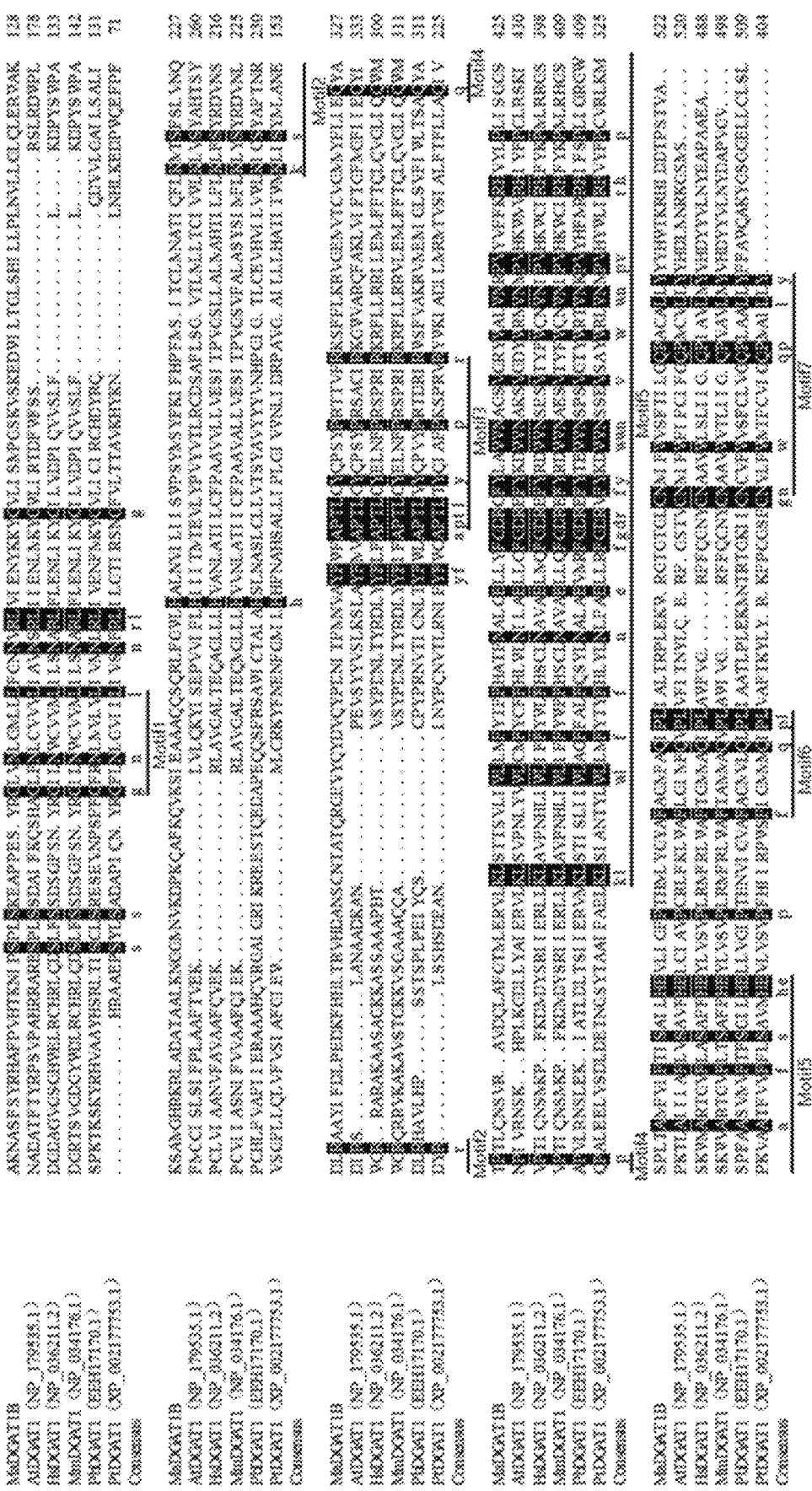
FIG. 1 is an amino acid sequence alignment result between MaDGAT1B and a known diacylglycerol acyltransferase 1.

The invention is further explained in details below with regard to specific examples.

The *Mortierella alpina* ATCC 32222 used in the following examples was purchased from the American Type Culture Collection (ATCC). *E. coli* DH5a, *Saccharomyces cerevisiae* (*S. cerevisiae*) auxotrophic strain INVSc1, and expression vector pYES2/NT C were purchased from Invitrogen. KOD plus high-fidelity DNA polymerase was purchased from Toyobo. Taq DNA polymerase was purchased from CWBIO. A reverse transcription kit (PrimeScript RT regent Kit with gDNA Eraser RR047A&R6110A) was purchased from Takara. A plasmid extraction kit was purchased from TIANGEN BIOTECH (BEIJING) CO., LTD. A fungal genomic DNA extraction kit was purchased from BioFlux. Restriction enzymes (EcoR I, Xba I), $T_4$ ligase, Trizol, a PCR product purification kit, a gel recovery kit, GeneRuler DNA Ladder Mix, PageRuler Prestained Protein Ladder, and antibodies (6×His-Tag Monoclonal Antibody, HRP-Goat Anti-Mouse IgG [H+L]) were purchased from Thermo. n-pentadecanoic acid (C15:0), glycerol tripalmitate, 20% (w/w) hydrochloric acid methanol, acid washed glass beads and salmon sperm were purchased from Sigma. An acrylamide/methylene bisacrylamide 40% solution (29:1), TEMED, DEPC water, Ampicillin antibiotics, amino-free yeast nitrogen source (YNB) and various amino acids were purchased from Shanghai Bioengineering Co., Ltd. A yeast extract and a tryptone were purchased from Oxoid. A thin layer chromatography silica gel plate was purchased from Rushan Taiyang Silica Gel Co., Ltd. Bovine serum albumin was purchased from Macklin. Low-adsorption RNase-free pipette tips, RNase-free centrifuge tubes, RNase-free PCR tubes, 2 mL brown gas bottles and bottle caps were purchased from Suzhou Keqing Biology Co., Ltd. BCA protein assay kits were purchased from Shanghai Beyotime Biotechnology. Glass spotting capillary tubes were purchased from Shanghai Shendi Glass Instrument Co., Ltd. Skimmed milk powder was purchased from BD, USA. PVDF membranes and Plus ECL developer were purchased from MILLIPORE. Other reagents were purchased from Sinopharm Group.

The reagents and formulas related to *Saccharomyces cerevisiae* (*S. cerevisiae*) transformation are based on the manual for pYES2 plasmid expression of Invitrogen, in which PEG-3350 was replaced by PEG-4000.

Primers used in the following examples were synthesized by Shanghai Sunny Biotechnology Co., Ltd., and the sequencing work was completed by BGI, Shanghai.

The *Mortierella alpina* ATCC 32222, the *E. coli* DH5a, and the *Saccharomyces cerevisiae* (*S. cerevisiae*) auxotrophic strain INVSc1 are all commercially available and do not need disposition for patent procedures)

The culture media used in the following examples are as follows:

LB liquid culture medium: 10 g/L tryptone, 5 g/L yeast extract, and 10 g/L NaCl.

LB solid culture medium: 10 g/L tryptone, 5 g/L yeast extract, 10 g/L NaCl, and 20 g/L agar.

SOC recovery culture medium: 20 g/L tryptone, 5 g/L yeast extract, 0.5 g/L NaCl, 0.186 g/L KCl, 0.95 g/L $MgCl_2$, and 3.6 g/L glucose.

YPD liquid culture medium: 10 g/L yeast extract, 20 g/L tryptone, and 20 g/L glucose.

YPD solid culture medium: 10 g/L yeast extract, 20 g/L tryptone, 20 g/L glucose, and 20 g/L agar.

SC-U liquid culture medium: 20 g/L glucose, 6.7 g/L YNB, 0.1 g/L amino acids each (adenine, arginine, cysteine, leucine, lysine, threonine and tryptophan), and 0.05 g/L amino acids each (aspartic acid, histidine, isoleucine, methionine, phenylalanine, proline, serine, tyrosine and valine).

SC-U solid culture medium: 20 g/L glucose, 6.7 g/L YNB, 0.1 g/L amino acids each (adenine, arginine, cysteine, leucine, lysine, threonine and tryptophan), 0.05 g/L amino acids each (aspartic acid, histidine, isoleucine, methionine, phenylalanine, proline, serine, tyrosine and valine), and 20 g/L agar.

SC-U induction culture medium: 10 g/L raffinose, 6.7 g/L YNB, 0.1 g/L amino acids each (adenine, arginine, cysteine, leucine, lysine, threonine and tryptophan), 0.05 g/L amino acids each (aspartic acid, histidine, isoleucine, methionine, phenylalanine, proline, serine, tyrosine and valine), and 20 g/L galactose.

Example 1. Screening and Bioinformatics Analysis of Gene Encoding Diacylglycerol Acyltransferase 1

Specific steps are as follows:

dgat1 gene sequences with identified functions in different species were selected from NCBI as templates (Table 1), and BLAST alignment was carried out in the gene bank of the *M. alpina* ATCC 3222 strain that had been sequenced to obtain candidate target genes. Then, the candidate genes were compared and screened for a second time in the NCBI library, the finally obtained target gene was named Madgat1b, and the corresponding protein was named MaDGAT1B.

Figure 2:
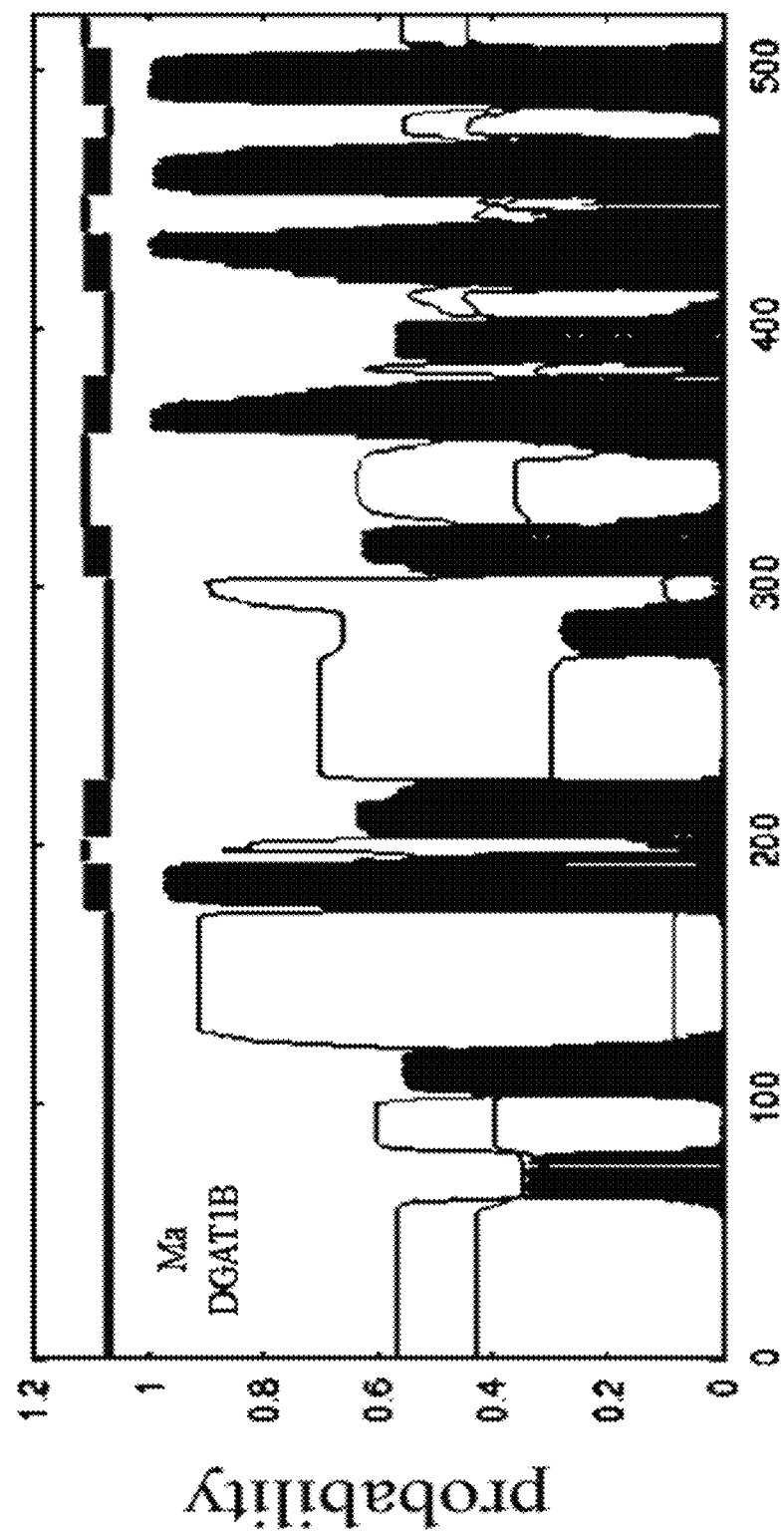
FIG. 2 is a prediction chart of a transmembrane structure of MaDGAT1B.

In order to determine whether the screened MaDGAT1B belongs to a DGAT1 enzyme, it was compared with amino acid sequences of 5 typical DGAT1s from animals, higher plants, microorganisms and microalgae in Table 1, and amino acid homology and conserved structure analysis were performed by DNAMAN software. The results are shown in FIG. 1 (black marked parts indicate the amino acids with 100% similarity). A transmembrane structure of MaDGAT1B was predicted through the online website TMHMM, and the results are shown in FIG. 2. In addition, the protein molecular weight and isoelectric point of MaDGAT1B were predicted through the online website ExPASy-ProtParam tool.

The research results show that there are 7 conserved domains in the DGAT1, respectively marked as Motif1-7. The corresponding conserved domains are as follows: Motif1 (GL segment), Motif2 (KSR segment), Motif3 (PTR segment), Motif4 (QP segment), Motif5 (LWLFFEFDRFYWWNWWNPPFSHP segment), Motif6 (FQL segment) and Motif7 (NGQPY segment). The DGAT1 generally has more than 500 amino acid residues with a molecular weight of 50-60 kD. The three-dimensional structure of the protein includes 6-9 hypothetical transmembrane regions.

It can be seen from FIG. 1 that the MaDGAT1B contains 7 conserved motifs (underlined parts) that the known DGAT1 enzymes normally have. The similarity between the MaDGAT1B with the DGAT1 proteins from 5 different sources in Table 1 is 37.48%. The full length of cDNA corresponding to MaDGAT1B is 1569 bp, which encodes 522 amino acids. It can be seen from FIG. 2 that the MaDGAT1B contains 7 transmembrane regions. In addition, based on the prediction results of the ExPASy-ProtParam tool, the protein molecular weight of the MaDGAT1B is about 59.49 kD and the isoelectric point is 9.43. Thus, the MaDGAT1B has characteristic features of a typical DGAT1 protein.

Based on the above results, the similarity of the amino acid sequences between the MaDGAT1B and the DGAT1s of different species is of biological significance, and the gene length, the number of amino acids, the conserved domains and the transmembrane regions all conform to the features of the DGAT1 enzyme, so it is believed that the screened MaDGAT1B has the function of the DGAT1 protein.

TABLE 1

List of dgat1 genes from different sources

| Type | Species | Abbreviation | Number |
|---|---|---|---|
| dgat1 | Homo sapiens | Hsdgat1 | NM_012079.6 |
|  | Mouse | Mmdgat1 | NM_010046.3 |
|  | Arabidopsis | Atdgat1 | NM_127503.3 |
|  | Phaeodactylum tricornutum | Ptdgat1 | XM_002177717.1 |
|  | Blastomyces brasiliensis | Pbdgat1 | KN305546.1 |

Example 2. Cloning of Madgat1b

Specific steps are as follows:

The total RNA of *Mortierella alpina* ATCC 32222 was extracted by a Trizol method, reverse transcription was performed according to instructions of the Takara reverse transcription kit to obtain a cDNA library, and a PCR reaction was carried out in the cDNA library of the *Mortierella alpina* ATCC 32222 to amplify Madgat1b cDNA. Primers used to amplify the Madgat1b are shown in Table 2.

The PCR instrument used was BIO-RAD T100 Thermal Cycler, KOD plus high-fidelity DNA polymerase was used, the reaction system was 50 µL, and the system is specifically carried out according to the DNA polymerase instructions. The reaction process was as follows: pre-denaturation was performed at 94° C. for 3 min, then denaturation was performed at 94° C. for 30 s, annealing was performed at 60° C. for 30 s, extension was performed at 68° C. for 100 s, the above three steps were repeated 30 times, then full extension was performed at 68° C. for 7 min, and finally, the temperature was dropped to 12° C. and held for 5 min before termination reaction.

After the completion of the reaction, the correct length of the amplification product band was verified by 1% agarose gel electrophoresis, and the PCR product was purified to obtain the Madgat1b cDNA.

TABLE 2

Primer sequences

| Primer Name | Primer Sequence (5'-3') | Uses |
|---|---|---|
| Madgat1b F | SEQ ID No. 3: CCGGAATTCATGACCAAGAACGAGCCC | For Madgat1b gene amplification |
| Madgat1b R | SEQ ID No. 4: CTAGTCTAGATCAGGCTACTGTCGAGGG |  |

Note:
The restriction sites are underlined.

Example 3. Expression of Madgat1b in *Saccharomyces Cerevisiae*

Specific steps are as follows:
(1) Construction of Yeast Expression Vector

Figure 3:
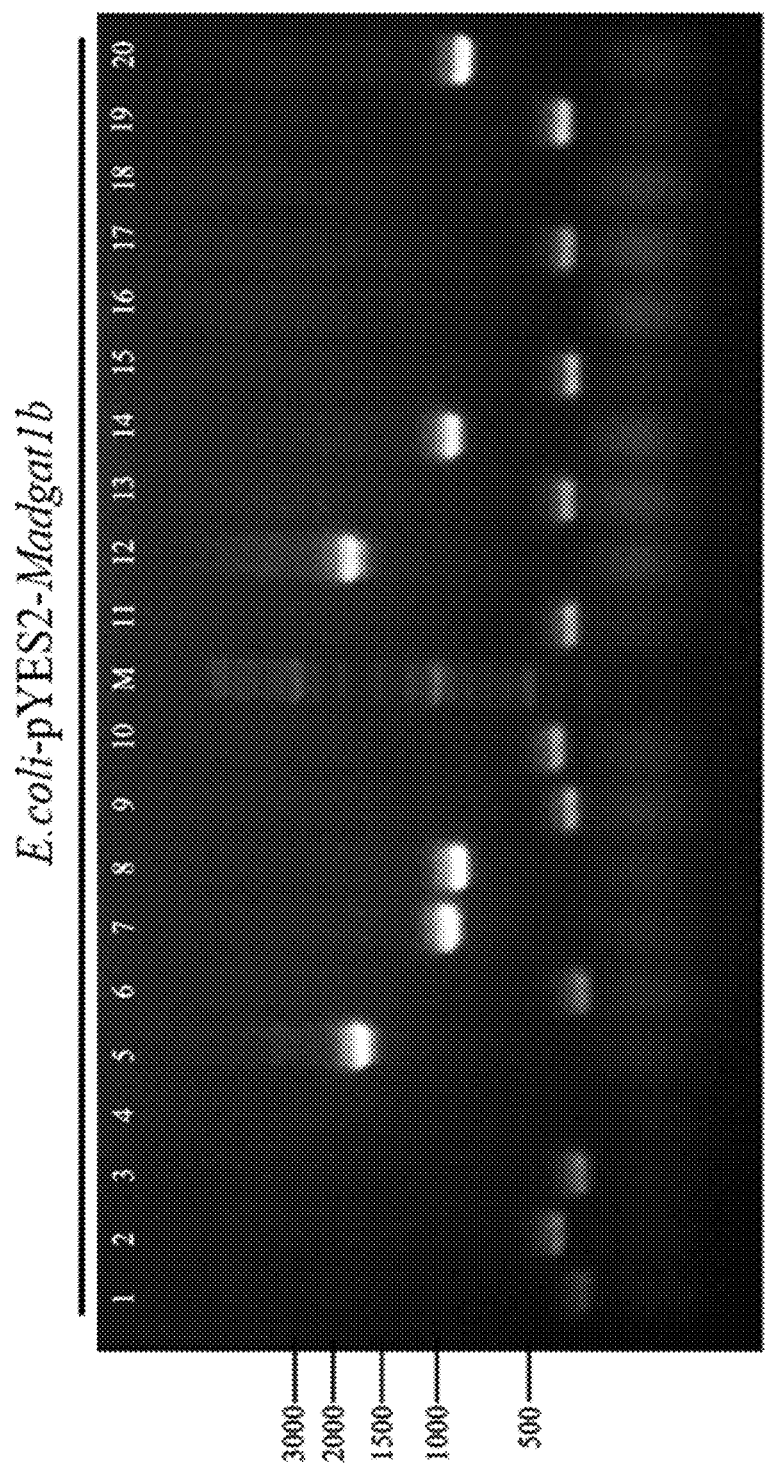
FIG. 3 is a verification diagram of positive transformants of recombinant *E. coli, E. coli*-pYES2-Madgat1b, where M represents a marker, and 1-20 respectively represent transformant numbers.

After the Madgat1b PCR product was digested with the restriction enzymes EcoR I and Xba I, the digestion product was ligated to a corresponding multiple cloning site downstream a (3-galactosidase (GALL) promoter in the pYES2/NT C expression vector by the $T_4$ ligase. The ligation product (not more than 5%) was introduced into *E. coli* DH5a by chemical transformation (under transformation conditions of 42° C. and 90 s), and preliminary screening was performed by using the LB agar medium plate with 0.1 g/L Ampicillin to obtain an *E. coli* positive transformant. Then the plasmid was extracted as a template, PCR amplification was carried out by using a universal primer T7/T7 terminator in Table 3, the product was verified by 1% agarose gel electrophoresis, and the *E. coli* positive transformants with correct band length were preliminarily screened out and subjected to sequencing analysis. After the successful sequencing, the recombinant plasmid was obtained, named pYES2-Madgat1b (the screening and verification results of the *E. coli* DH5a positive transformants are shown in FIG. 3, the length of the Madgat1b amplified by the universal primer should be 1917 bp since the replication was started from the pYES2 vector, FIG. 3 shows that the transformants 5 and 12 of the *E. coli*-pYES2-Madgat1b have target bands at about 2000 bp, and after the transformant *E. coli*-pYES2-Madgat1b-12 was further verified by sequencing, the sequencing results were consistent with the theoretical values).

(2) Transformation and Screening of *Saccharomyces cerevisiae*

Figure 4:
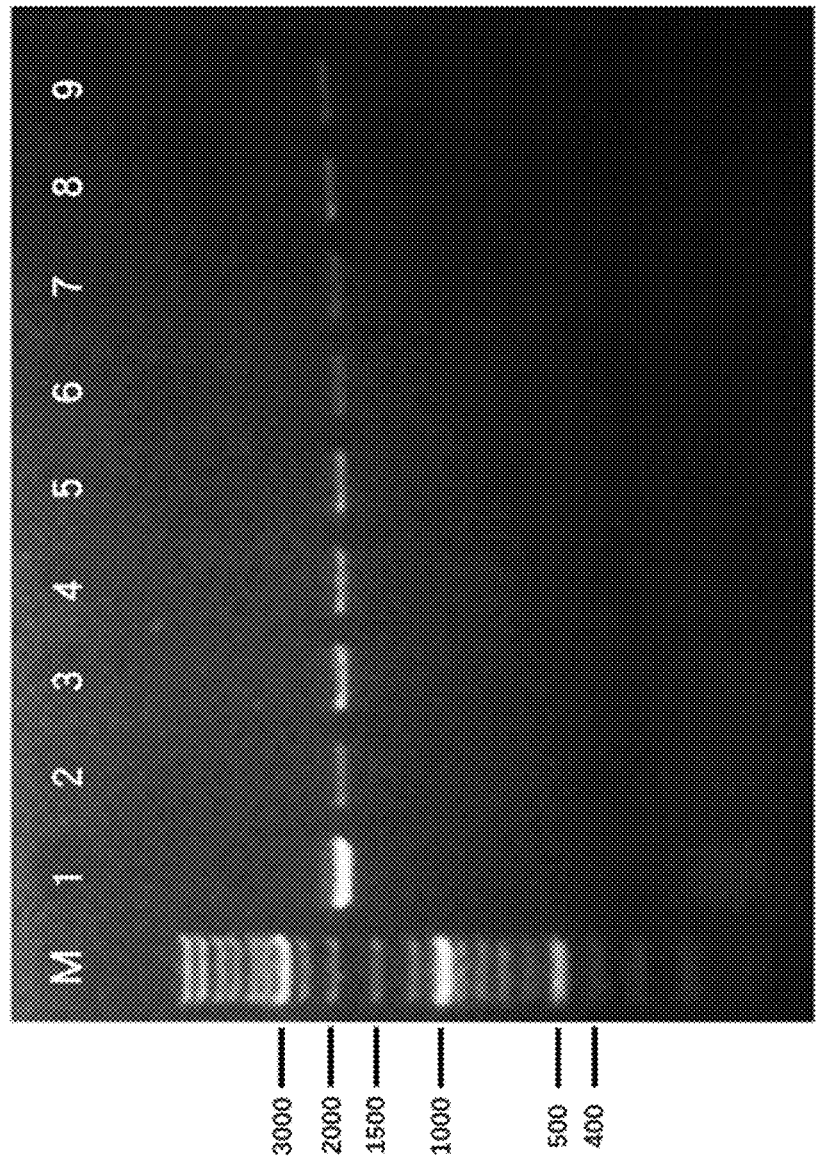
FIG. 4 is a verification diagram of positive transformants of recombinant *Saccharomyces cerevisiae* INVSc1-pYES2-Madgat1b, where "M" represents a marker, and 1-9 respectively represent transformant numbers.

According to the pYES2 plasmid manual of Invitrogen, the recombinant plasmid pYES2-Madgat1b with correct sequence obtained in (1) and the empty vector pYES2/NT C (used as a negative control) were respectively transformed into the *Saccharomyces cerevisiae* strain INVSc1 by PEG/LiAc method, and preliminary screening was carried out by using the SC-U solid culture medium plate without ura⁻ to obtain *Saccharomyces cerevisiae* positive transformants. Then the yeast genome was extracted as a template, PCR amplification was carried out by using the universal primer T7/T7 terminator in Table 3, the product was verified by 1% agarose gel electrophoresis, and the positive transformants with correct band length were preliminarily screened out and subjected to sequencing analysis to obtain recombinant *Saccharomyces cerevisiae* INVSc1-pYES2-Madgat1b and recombinant *Saccharomyces cerevisiae* INVSc1-pYES2. The screening verification results of the *Saccharomyces cerevisiae* positive transformants were shown in FIG. 4. It can be seen from FIG. 4 that the transformants 1-9 of the INVSc1-pYES2-Madgat1b have PCR products with expected length of about 2000 bp. The transformants 1-9 of the INVSc1-pYES2-Madgat1b were further verified by sequencing with results consistent to the expected nucleotide sequence.

(3) Induction Culture

The recombinant *Saccharomyces cerevisiae* INVSc1-pYES2-Madgat1b and the recombinant *Saccharomyces cerevisiae* INVSc1-pYES2 were cultured in the SC-U liquid culture medium at 28° C., 200 rpm for 48 h, and after centrifugation at 6000 rpm for 5 min, the culture medium was discarded and the cells was inoculated (initial $OD_{600}$=0.4) into the SC-U induction culture medium containing galactose, but no glucose, to induce the expression of the Madgat1b. Culture was carried out for 48 h under the same conditions to obtain a fermentation broth. The fermentation broth was centrifuged at 12000 rpm for 1 min to collect cells. Part of the wet cells were taken for protein expression analysis. The rest of the cells were freeze-dried, and the biomass, and the lipid components and contents were determined.

(4) Determination of Expression Level of Target Protein 2 mL of the fermentation broth after 48 h of induction was collected, and centrifuged at 12000 rpm, 4° C. for 1 min to collect cells. The *Saccharomyces cerevisiae* whole cell protein was extracted based on the pYES2 plasmid manual of Invitrogen. A lysate was added to the cells such that the $OD_{600}$ value reached 50-100. Then 0.5 mm acid washed glass beads of the same volume as the lysate were added. The mixture was shaken in a vortex shaker for 30 seconds and placed on ice for 30 seconds. The whole cell protein extract was obtained after repeating 4 times of the above operation. The protein concentration of the whole cell protein extract was determined by using a BCA kit. The sample was separated through SDS-PAGE (10% separation gel), and electrotransferred (200 mA, 1 h) onto a PVDF membrane. An anti-his antibody with a dilution of 1:2000 was used as the primary antibody, and a mouse secondary antibody with a dilution of 1:5000 was used to bind to the aforementioned primary antibody, and then reacts with a chemiluminescent solution to develop chemiluminescent products, and photographing were carried out with an imager.

The expression of the target protein MaDGAT1B in the yeast recombinant strain was analyzed by Western Blot. The 6×his tag at the N-terminus of the pYES2/NT C vector was selected as the antigen, and the molecular weight of the 6×his-tagged MaDGAT1B protein was about 64 kD as predicted with an online software ExPASy-ProtParam tool. The Western Blot results are shown in FIG. 5.

Figure 5:
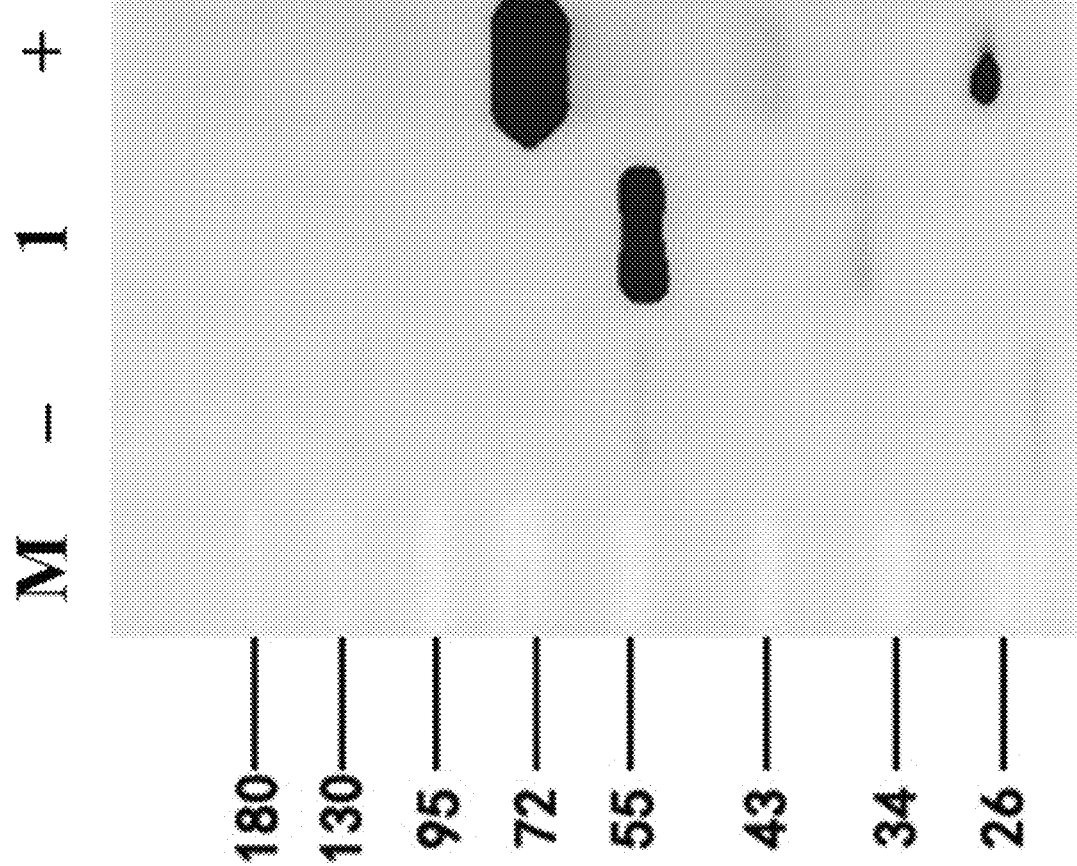
FIG. 5 is a verification diagram of expression of target protein MaDGAT1B of the recombinant *Saccharomyces cerevisiae* INVSc1-pYES2-Madgat1b, where "M" represents a marker, "−" represents negative control (INVSc1-pYES2 empty vector), "+" represents positive control (other INVSc1-pYES2 with his-tagged proteins), and "1" represents INVSc1-pYES2-Madgat1b.

It can be seen from FIG. 5 that the whole protein extract of the INVSc1-pYES2-Madgat1b contains a protein that binds to the anti-his antibody and has a molecular mass of 55-72 kD, which is consistent with the expected molecular weight 64 kD of the target protein. Thus, the band is 6×his-tagged MaDGAT1B, indicating that the foreign protein MaDGAT1B can be successfully expressed in *Saccharomyces cerevisiae* INVSc1-pYES2-Madgat1b.

The whole cell protein extract of INVSc1-pYES2-Madgat1b was centrifuged at 20000 g for 15 min, and the supernatant and the precipitate were taken for protein concentration determination. Finally, the whole cell protein extract (20 μg protein) and the protein precipitate (20 μg protein) were respectively taken for Western Blot experiments (no experiment was performed for the supernatant due to low protein concentration), and the protein expression was estimated by Image J software. The results are shown in FIG. 6-FIG. 7.

Figure 6:
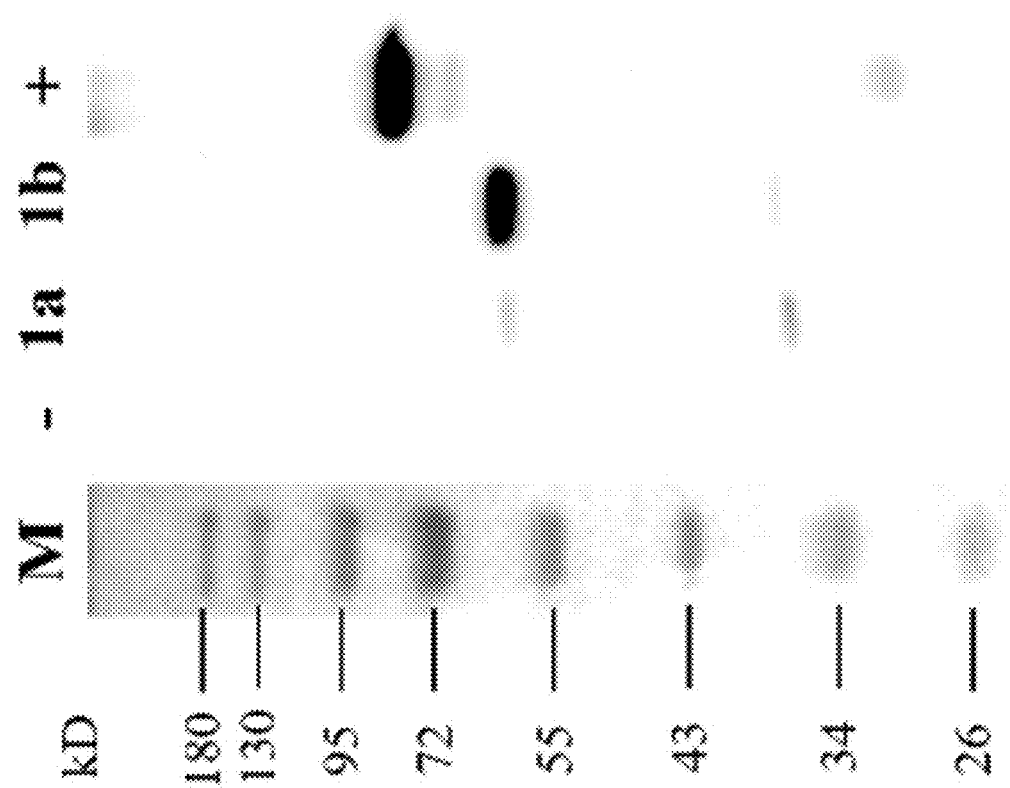
FIG. 6 shows Western Blot results of expression of target protein MaDGAT1B in recombinant *Saccharomyces cerevisiae* INVSc1-pYES2-Madgat1b whole cell protein and whole cell protein precipitate, where "M" represents a marker, "−" represents negative control (INVSc1-pYES2 empty vector), "+" represents positive control (other INVSc1-pYES2 with his-tagged proteins), "1a" represents INVSc1-pYES2-Madgat1b whole cell protein, and "1b" represents INVSc1-pYES2-Madgat1b whole cell protein precipitate.
Figure 7:
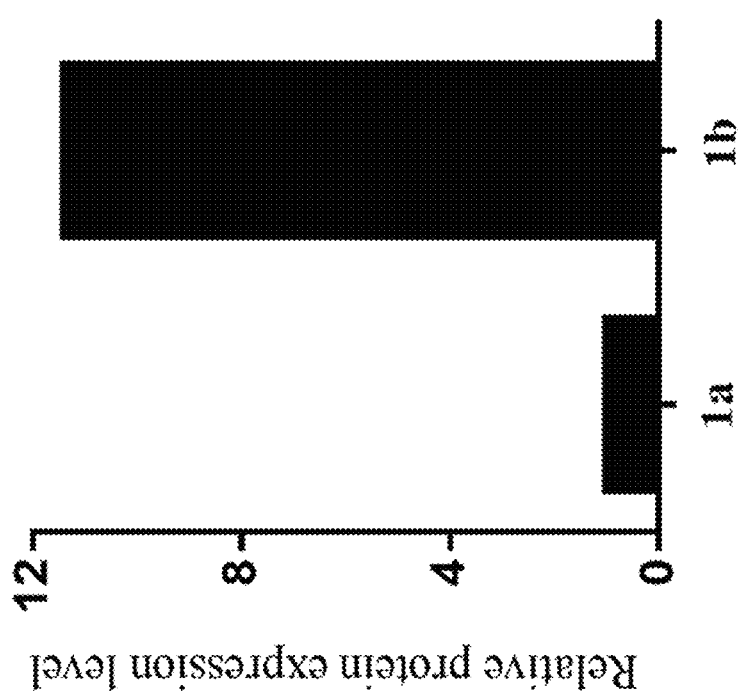
FIG. 7 shows grey-scale analysis of expression of target protein MaDGAT1B in the recombinant *Saccharomyces cerevisiae* INVSc1-pYES2-Madgat1b whole cell protein and whole cell protein precipitate, where "1a" represents INVSc1-pYES2-Madgat1b whole cell protein, and "1b" represents INVSc1-pYES2-Madgat1b whole cell protein precipitate.

It can be seen from FIG. 6-FIG. 7 that a strong signal of his-tagged MaDGAT1B is detected in the precipitate, but the amount of his-tagged MaDGAT1B in the cell whole cell protein sample is significantly reduced, with a difference of about 11 times. It is speculated that the phenomenon may be due to the fact that the MaDGAT1B is an endoplasmic reticulum membrane protein, which precipitates with organelle fragments during centrifugation.

(5) Determination of Composition and Contents of Fatty Acids in Triacylglycerol

Thin layer chromatography (TLC) is a method to separate components of a mixture based on their different distribution or retention rates between the stationary phase and the mobile phase of the TLC. The components are developed and colored to form chromatographic bands, and the bands can be treated by a proper technique to obtain qualitative and quantitative detection results. Therefore, the thin layer chromatography was used to separate TAG from the total lipids of the cells obtained in (3), and the fatty acid composition and contents of the TAG were detected by a GC-MS technique.

Specific steps are as follows:

20 mg of cells was weighed into a lipid extraction glass bottle, the total lipids were extracted with a mixed organic reagent of chloroform:methanol:water=2:2:1 (v/v/v), various lipids were separated on a thin layer chromatography plate by using a mixed solvent of n-hexane:diethyl ether:acetic acid=80:20:1 (v/v/v) as a developing solvent, spots were visualized with iodine fuming, and grey-scale analysis was carried out using Image J software to estimate the proportion of TAG in total fatty acids. Then, the spots of the TAG were immediately scraped off and placed in the lipid extraction glass bottle, followed by the addition of a pentadecanoic acid standard as an internal standard. Methyl esterification was carried out in a 60° C. water bath for 3 hours by using a solvent of hydrochloric acid:methanol=1:9 (w/w). Fatty acid methyl ester was extracted with n-hexane. The fatty acid composition and contents in TAG were analyzed by a Shimadzu single quadrupole gas chromatography-mass spectrometer GC MS-QP2010 Ultra.

Operating conditions were as follows: a Rtx-Wax gas chromatography column (30 m×0.25 mm×0.25 μm) of RESTEK was used, helium was used as the carrier gas, the injection port temperature was 240° C., the injection volume was 1 μL, and the split ratio was 10. The temperature of the column oven was started from 150° C. and held for 2 min, then raised to 190° C. at a rate of 10° C./min and held for 5 min, and then raised to 220° C. at a rate of 5° C./min and held for 16 min. The scanning range of the mass spectrometer was 50-550 m/z. The temperatures of the ion source and transmission line port were respectively 220° C. and 250° C.

Figure 8:
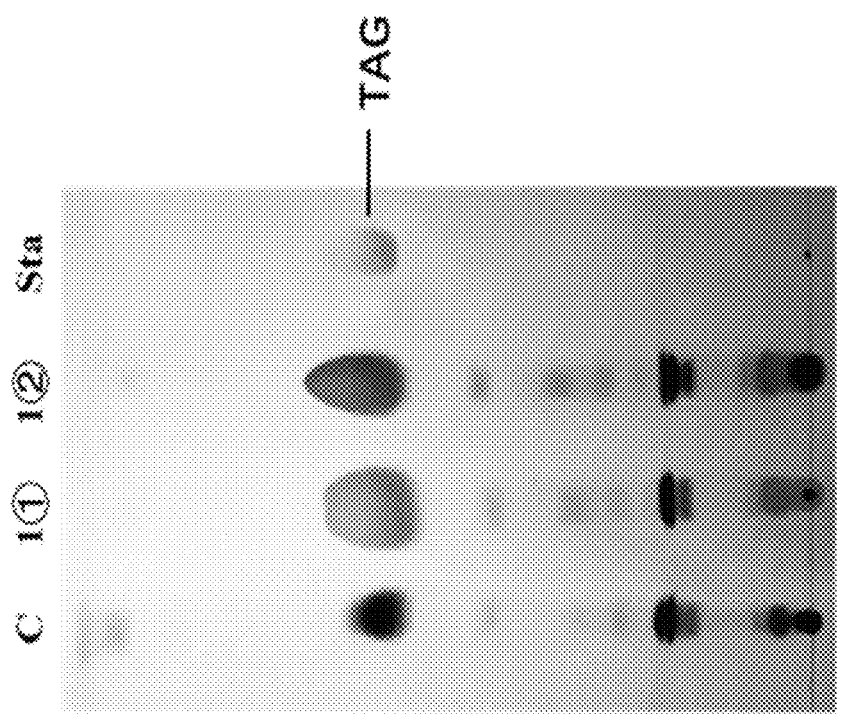
FIG. 8 is a thin-layer chromatogram of total lipids of the recombinant *Saccharomyces cerevisiae* INVSc1-pYES2-Madgat1b, where "C" represents 1NVSc1-pYES2, 1①and 1② represent two parallel groups of INVSc1-pYES2-Madgat1b, and "Sta" represents a triacylglycerol tripalmitate standard.
Figure 9:
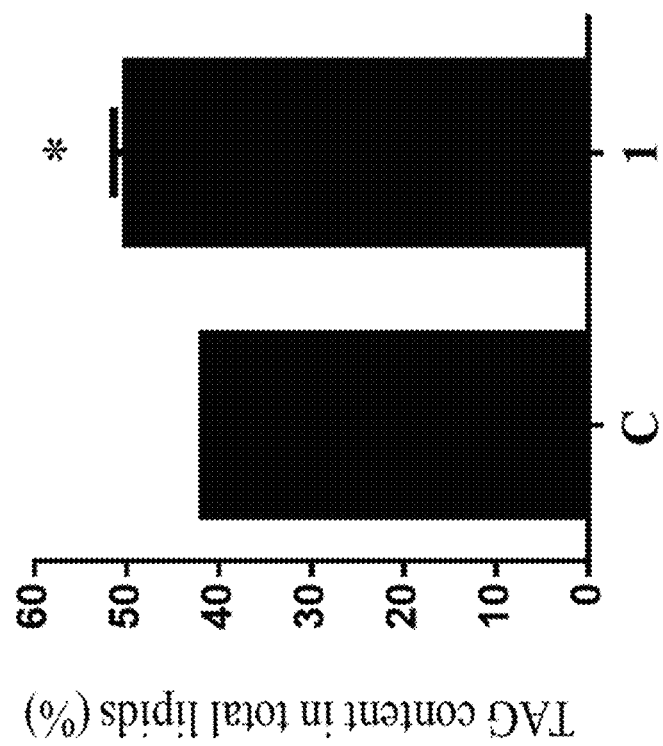
FIG. 9 shows contents of TAG in total fatty acids (TFA) of the recombinant *Saccharomyces cerevisiae* INVSc1-pYES2-Madgat1b, where "C" represents 1NVSc1-pYES2, and "1" represents INVSc1-pYES2-Madgat1b.

The distribution patterns and quantitative analysis of total fatty acids in the recombinant strains detected by TLC are shown in FIG. 8-FIG. 9. It can be seen from FIG. 8-FIG. 9 that the TAG content in 1NVSc1-pYES2, the control group, accounts for 42% of the total fatty acids; and compared with the control group, the TAG/TFA ratio in INVSc1-pYES2-Madgat1b changes significantly (p<0.05), and is 19.63% higher than that in the control group. It can be seen that Madgat1b shows strong ability to increase the content of TAG in total lipids.

After the sample of the TAG on the TLC plate was scraped and fatty acids were qualitatively and quantitatively analyzed by GC-MS. The results of composition and contents of fatty acids in TAG are shown in FIG. 10.

Figure 10:
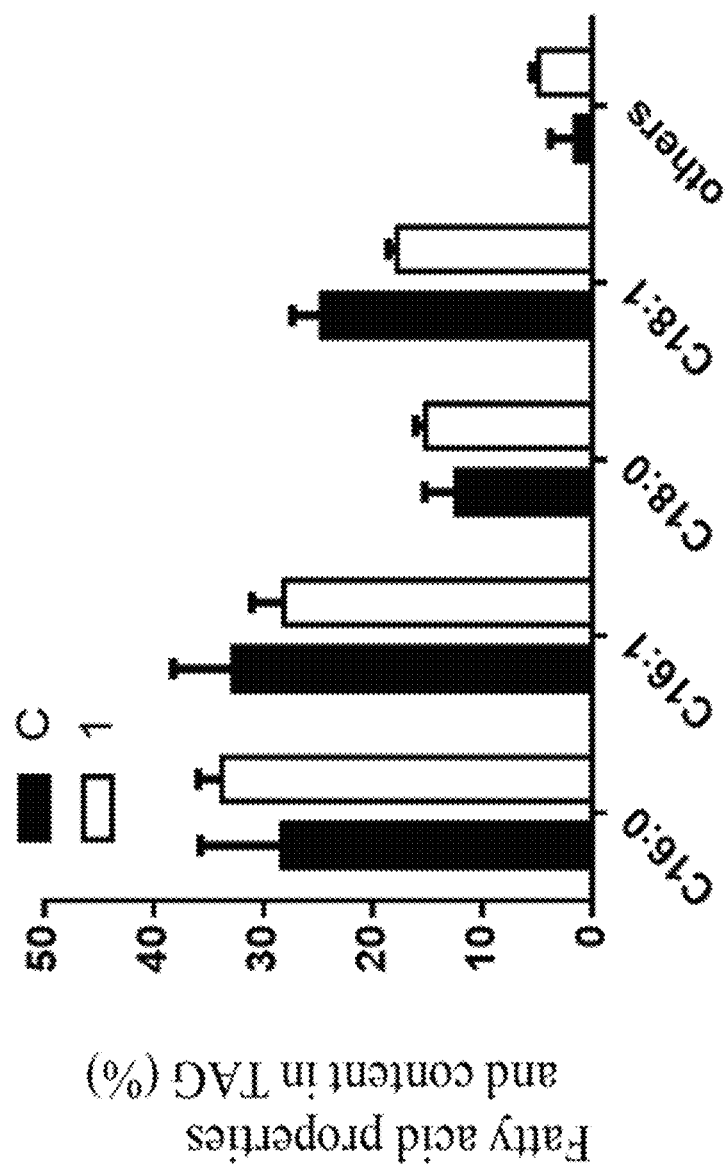
FIG. 10 shows composition and contents of fatty acids in TAG of the recombinant *Saccharomyces cerevisiae* INVSc1-pYES2-Madgat1b, where "C" represents 1NVSc1-pYES2, "1" represents INVSc1-pYES2-Madgat1b, and "other" represents the sum of contents of fatty acids other than C16:0, C16:1, C18:0 and C18:1.

It can be seen from FIG. 10 that the main fatty acid components of TAG in *Saccharomyces cerevisiae* are hexadecanoic acid (C16:0), hexadecenoic acid (C16:1), octadecanoic acid (C18:0) and octadecenoic acid (C18:1), and compared with the control group, there is no significant change in the ratios of fatty acid components in the MaDGAT1B transformants.

Figure 11:
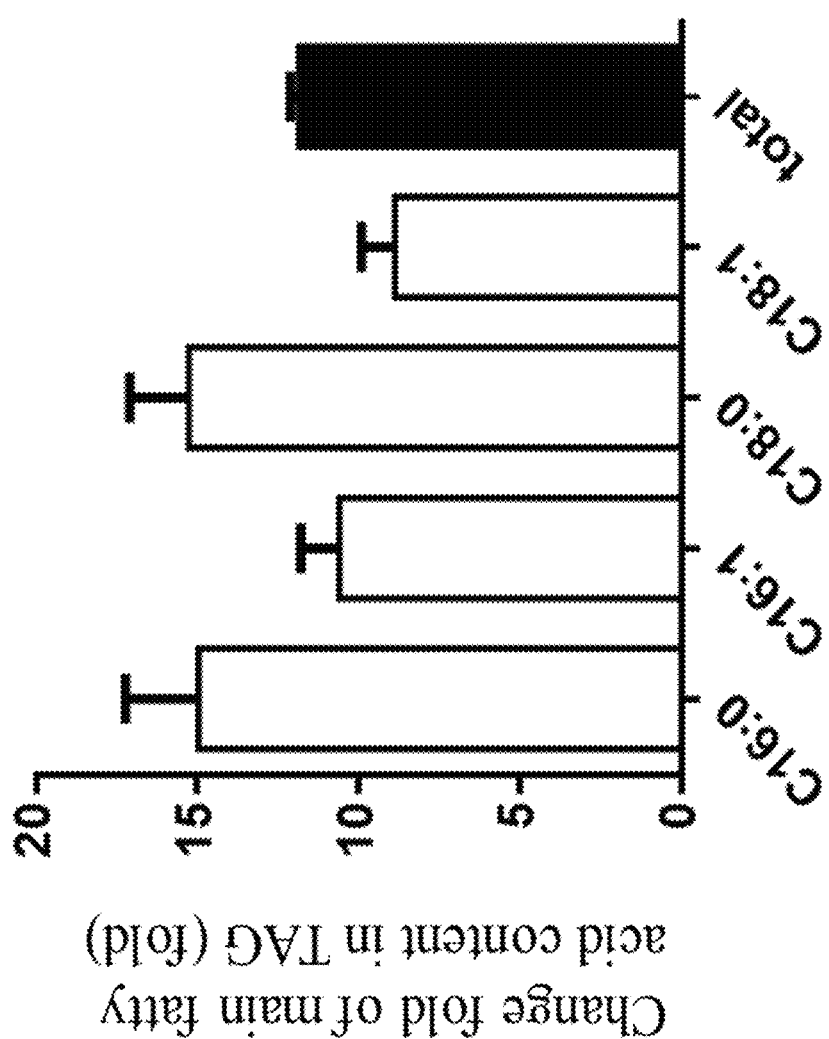
FIG. 11 shows changes in the content of main fatty acids in the TAG of the recombinant *Saccharomyces cerevisiae* INVSc1-pYES2-Madgat1b, where the y-ordinate represents a ratio of the fatty acid content in INVSc1-pYES2-Madgat1b vs. INVSc1-pYES2.

The contents of four main TAG fatty acids of the INVSc1-pYES2-Madgat1b transformant were compared with those of the control group, and the results are shown in FIG. 11. It can be seen from FIG. 11 that the contents of the four main TAG fatty acids of the INVSc1-pYES2-Madgat1b are significantly increased as compared to those of the control group, and the contents of C16:0, C16:1, C18:0 and C18:1 are respectively increased by 15.24, 10.36, 15.21 and 9.14 folds, resulting in a total increase of TAG 12.09 folds than that of the control group. It can be seen that the Madgat1b has significant effects in increasing the content of TAG, and has great potential in increasing the lipid content of oleaginous microorganisms.

(6) Determination of Composition and Contents of Total Fatty Acids in Cells 20 mg of freeze-dried 1NVSc1-pYES2 and INVSc1-pYES2-Madgat1b cells were respectively weighed into a lipid extraction glass bottle. 2 mL of hydrochloric acid with a concentration of 4 mol/L was added. After being in a water bath at 80° C. for 1 h, the mixture was sufficiently shaken and allowed to stand in a −80° C. refrigerator for 15 min. The above freezing and thawing operations were repeated for 3 times, followed by the addition of 100 μL of 2.096 mg/mL pentadecanoic acid standard as an internal standard. Lipids were extracted with 1 mL of chloroform and 1 mL of methanol. After rotation shaking for 1 h, centrifugation was carried out at 2000 rpm, the lower chloroform layer was pipetted into a new bottle, 1 mL of chloroform was added, and the mixture was sufficiently shaken. The same operations were repeated for one more time. The two chloroform layers were combined and blow-dried with nitrogen. Subsequent methyl esterification and determination methods were the same as described in (5).

Figure 12:
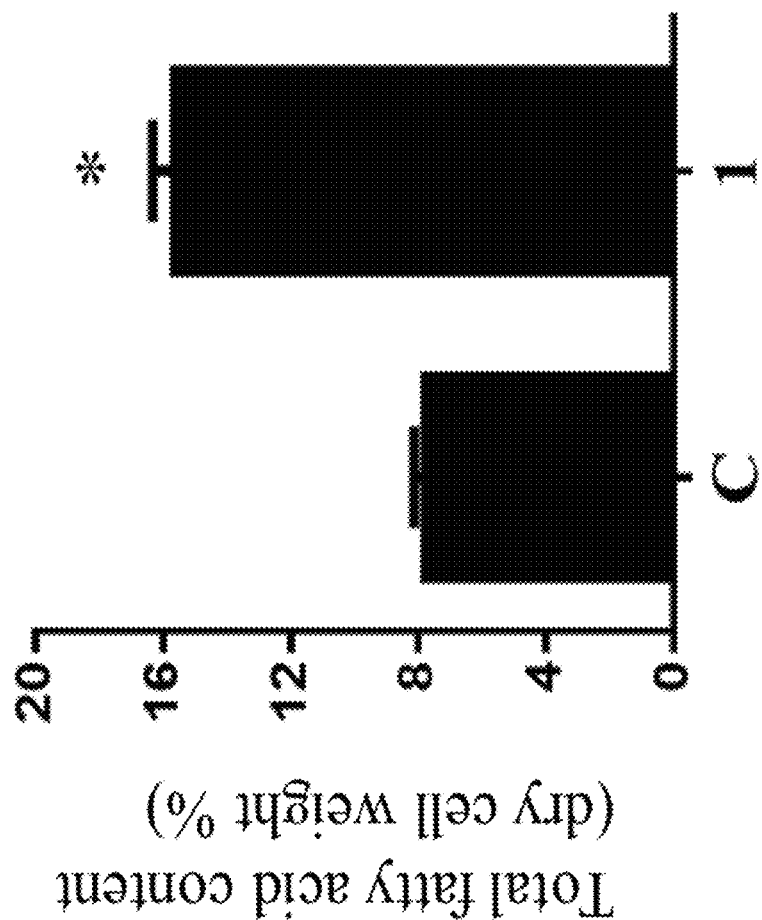
FIG. 12 shows a total fatty acid content of the recombinant *Saccharomyces cerevisiae* INVSc1-pYES2-Madgat1b, where "C" represents 1NVSc1-pYES2, and "1" represents INVSc1-pYES2-Madgat1b.
Figure 13:
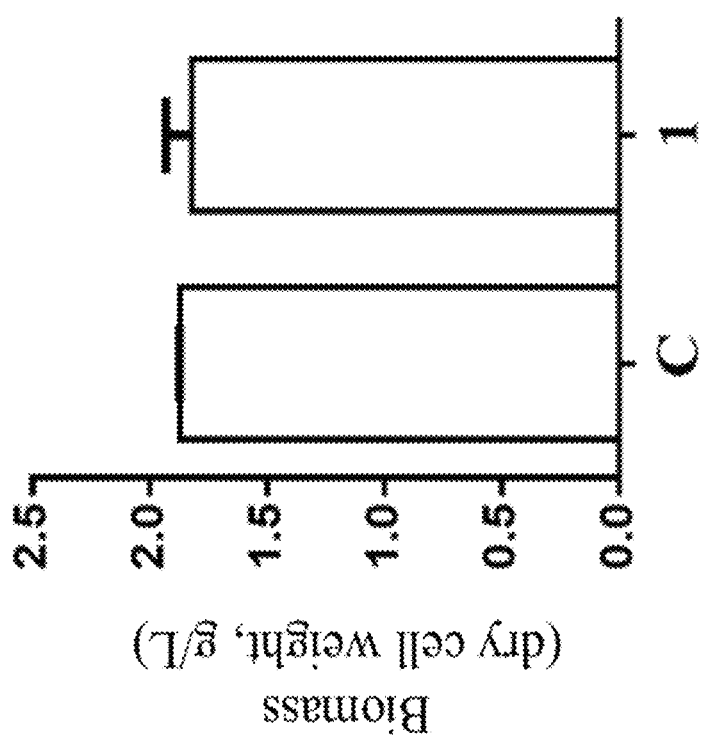
FIG. 13 shows biomass (dry cell weight) of the recombinant *Saccharomyces cerevisiae* INVSc1-pYES2-Madgat1b, where C represents 1NVSc1-pYES2, 1 represents INVSc1-pYES2-Madgat1b, and DCW represents dry cell weight.

The total fatty acid contents in the recombinant yeast strains are shown in FIG. 12. The biomass of the cells (dry cell weight per liter of culture medium) is shown in FIG. 13. The composition and contents of total fatty acids are shown in Table 4. It can be seen from FIG. 12-FIG. 13 that compared with the control group 1NVSc1-pYES2, the expression of the exogenous MaDGAT1B in *Saccharomyces cerevisiae* has no significant effect on the growth of cells. The total fatty acid content in the *Saccharomyces cerevisiae* of the control group was 7.79% of the dry cell weight, and the total fatty acid content in the INVSc1-pYES2-Madgat1b was 15.15% of the dry cell weight, which was significantly increased by 1.94 times as compared with that of the control group ($p<0.05$).

It can be seen from Table 4 that the contents of fatty acids in the INVSc1-pYES2-Madgat1b are all greatly increased. The C14:0 increased the most, which was 5.79 times of the control group, but the proportion of C14:0 in total fatty acids was relatively low, and thus has less effect on the total fatty acid content. The contents of the C16:0, C16:1, C18:0 and C18:1 are respectively increased by 2.40, 1.61, 2.91 and 1.63 times, respectively, accounting for 25.33%, 31.55%, 13.50% and 23.58% of the total fatty acids. Therefore, they are the main fatty acid components causing the increase of the total fatty acid content.

It can be seen that the expression of Madgat1b can significantly increase the total fatty acid content, indicating that the DGAT1 protein from *Mortierella alpina* can lead to more lipid production and accumulation and has good application values.

TABLE 3

Primer sequences

| Primer Name | Primer Sequence (5'-3') | Uses |
| --- | --- | --- |
| T7 | SEQ ID No. 5: TAATACGACTCACTATAGGG | To verify recombinant plasmids constructed using a pYES2/NT C vector |
| T7 terminator | SEQ ID No. 6: TCGGTTAGAGCGGATGTG | |

TABLE 4

Composition and contents of total fatty acids in *Saccharomyces cerevisiae*

| Strain | Contents of Various Fatty Acids (%, w/w, dry cell weight) | | | | | | | |
| --- | --- | --- | --- | --- | --- | --- | --- | --- |
| | C12:0 | C14:0 | C14:1 | C16:0 | C16:1 | C18:0 | C18:1 | C26:0 |
| C | 0.04 ± 0.00 | 0.06 ± 0.00 | 0.02 ± 0.00 | 1.60 ± 0.02 | 2.97 ± 0.04 | 0.70 ± 0.02 | 2.19 ± 0.03 | 0.20 ± 0.15 |
| 1 | 0.12 ± 0.00 | 0.36 ± 0.00 | 0.07 ± 0.00 | 3.84 ± 0.16 | 4.77 ± 0.02 | 2.05 ± 0.14 | 3.57 ± 0.08 | 0.36 ± 0.11 |

Note:
C is INVSc1-pYES2 *Saccharomyces cerevisiae*, and 1 is INVSc1-pYES2-Madgat1b *Saccharomyces cerevisiae*.

Although the invention has been disclosed above in some specific embodiments, it is not intended to limit the scope of the invention. One skilled in the art can make various changes and modifications without departing from the spirit and scope of the invention. Therefore, the scope of the invention should be defined in the claims.

What is claimed is:

1. A recombinant *Saccharomyces cerevisiae* expressing diacylglycerol acyltransferase 1, wherein the recombinant *Saccharomyces cerevisiae* carries a recombinant vector pYES2-Madgat1b, wherein the recombinant vector pYES2-MadgatIb is constructed by connecting a gene encoding the diacylglycerol acyltransferase 1 of SEQ ID NO: 1 to vector pYES2.

2. The recombinant *Saccharomyces cerevisiae* of claim 1, wherein the *Saccharomyces cerevisiae* is *Saccharomyces cerevisiae* INVSc1.

3. A method of preparing diacylglycerol acyltransferase 1, using the recombinant *Saccharomyces cerevisiae* of claim 1, comprising:

a) culturing the recombinant *Saccharomyces cerevisiae* of claim 1 in a culture medium without urea for 36-48 h;
b) adding the *Saccharomyces cerevisiae* cells of step a) to a culture medium without glucose and with galactose, and culturing until $OD_{600}$=0.3-0.5; and
c) continuing induction culture for 48-96 h to obtain the diacylglycerol acyltransferase 1.

4. The method of claim 3, wherein the culture medium of step a) and step b) is an SC-U culture medium.

5. The method of claim 4, wherein the culture of step a) and step b) is carried out at a temperature of 28-30° C. and at a rotation speed of 200-250 rpm.

6. A method for producing triacylglycerol, using the recombinant *Saccharomyces cerevisiae* according to claim 1, comprising:

a) culturing the recombinant *Saccharomyces cerevisiae* of claim 1 in a culture medium without urea for 36-48 h;
b) adding the *Saccharomyces cerevisiae* cells of step a) to a culture medium without glucose and with galactose, and culturing until $OD_{600}$=0.3-0.5; and
c) continuing induction culture for 48-96 h to obtain the triacylglycerol.

7. The method of claim 6, wherein the culture medium of step a) and step b) comprises an SC-U culture medium; and the culture of step a) and step b) is carried out at a temperature of 28-30° C. and at a rotation speed of 200-250 rpm.

* * * * *

SEQUENCE LISTING

<160> NUMBER OF SEQ ID NOS: 6

<210> SEQ ID NO 1
<211> LENGTH: 522
<212> TYPE: PRT
<213> ORGANISM: Mortierella alpina

<400> SEQUENCE: 1

```
Met Thr Lys Asn Glu Pro Val Leu Ala Ala Asp Val Ala Glu Ala Thr
1               5                  10                  15

Leu Pro Glu Ile Pro Pro Thr Val Glu Asp Leu Lys Lys Ala Lys Asn
            20                  25                  30

Ala Ser Phe Ser Tyr Arg His Ala Phe Pro Val His Thr Lys Asn Ile
        35                  40                  45

Pro Ser Pro Leu Ser Lys Glu Ala Pro Pro Glu Ser Tyr Arg Gly Leu
    50                  55                  60

Val Asn Leu Gly Met Leu Leu Phe Gly Asn Asn Val Arg Leu Val
65                  70                  75                  80

Ile Glu Asn Tyr Lys Lys Tyr Gly Val Leu Ile Ser Met Pro Gly Ser
                85                  90                  95

Lys Val Ser Lys Glu Asp Trp Ile Leu Thr Gly Leu Ser His Ile Leu
            100                 105                 110

Leu Pro Leu Asn Val Leu Leu Gly Leu Gln Leu Glu Arg Trp Ala Lys
        115                 120                 125

Lys Ser Ala Met Gly His Arg Lys Arg Leu Ala Asp Ala Thr Ala Ala
    130                 135                 140

Leu Lys Asn Gly Gly Met Asn Val Lys Asp Pro Lys Gln Ala Phe Lys
145                 150                 155                 160

Gln Val Lys Ser Ile Glu Ala Ala Gln Gln Ser Gln Arg Leu Phe
                165                 170                 175

Gly Trp Leu His Ala Leu Asn Val Ile Leu Ile Ser Trp Pro Ser
            180                 185                 190

Tyr Met Ser Tyr Phe Lys Ile Phe His Pro Phe Met Ser Ile Thr Cys
        195                 200                 205

Leu Met Asn Ala Thr Ile Gln Phe Leu Lys Met Thr Ser Phe Ser Leu
    210                 215                 220

Val Asn Gln Asp Leu Arg Ala Ala Tyr Ile Phe Asp Leu Pro Glu Asp
225                 230                 235                 240

Lys Phe His His Leu Thr Arg Val His Asp Ala Asn Ser Gly Asn Thr
                245                 250                 255

Ala Thr Gln Arg Gly Glu Val Tyr Gln Tyr Asp Val Gln Tyr Pro Asp
            260                 265                 270

Asn Ile Thr Phe Met Asn Val Ala Tyr Phe Trp Phe Ala Pro Thr Leu
        275                 280                 285

Cys Tyr Gln Pro Ser Tyr Pro Arg Thr Thr Val Phe Arg Lys Ser Phe
    290                 295                 300

Phe Leu Lys Arg Val Gly Glu Met Val Thr Cys Val Gly Met Met Tyr
305                 310                 315                 320

Phe Leu Ile Glu Gln Tyr Ala Thr Pro Thr Leu Gln Asn Ser Val Arg
                325                 330                 335

Ala Val Asp Gln Leu Ala Phe Gly Thr Met Leu Glu Arg Val Leu Lys
            340                 345                 350

Leu Ser Thr Thr Ser Val Leu Ile Trp Leu Leu Met Phe Tyr Thr Phe
        355                 360                 365
```

```
Phe His Ala Thr Phe Asn Ala Leu Gly Glu Leu Leu Tyr Phe Gly Asp
    370                 375                 380

Arg Cys Phe Tyr Leu Ala Trp Trp Asn Ala Gly Ser Val Gly Arg Tyr
385                 390                 395                 400

Trp Ala Leu Trp Asn Arg Pro Val Tyr Val Phe Phe Lys Arg His Val
                405                 410                 415

Tyr Leu Pro Leu Ile Ser Gly Gly Ser Ser Pro Leu Thr Ala Met Phe
                420                 425                 430

Val Ile Phe Thr Ile Ser Ala Ile Leu His Glu Val Leu Ile Gly Phe
            435                 440                 445

Pro Thr His Met Leu Tyr Gly Tyr Ala Phe Ala Gly Met Phe Ala Gln
    450                 455                 460

Ile Pro Leu Ile Ala Leu Thr Arg Pro Leu Glu Lys Trp Arg Gly Thr
465                 470                 475                 480

Gly Thr Gly Leu Gly Asn Met Ile Phe Trp Val Ser Phe Thr Ile Leu
                485                 490                 495

Gly Gln Pro Ala Cys Ala Leu Leu Tyr Tyr Tyr His Trp Thr Lys Arg
                500                 505                 510

His Ile Asp Asp Thr Pro Ser Thr Val Ala
                515                 520
```

<210> SEQ ID NO 2
<211> LENGTH: 1569
<212> TYPE: DNA
<213> ORGANISM: Mortierella alpina

<400> SEQUENCE: 2

```
atgaccaaga acgagcccgt tttggcagca gacgtcgctg aagctaccct ccccgagatc     60
ccgccaacag tcgaggatct caaaaaagct aaaaacgcaa gcttctcgta tcggcatgct    120
ttccccgtcc ataccaagaa catcccgagc ccctgtcga aggaagcgcc gccagagagt     180
tatagaggcc tcgtcaacct cgggatgctg cttctattcg caacaacgt tcggttggtg     240
atagagaact ataagaagta tggagttctg atctccatgc ctggatcaaa ggtttcgaag    300
gaggactgga tcctgacagg tctctcccac attctgttgc ccttgaatgt tcttttgggg    360
cttcagttgg agcgctgggc aaagaagagt gccatgggtc atcgcaaacg cctcgctgac    420
gctactgcag ctctcaagaa cggaggcatg aatgtcaagg accccaagca ggctttcaag    480
caggttaaaa gcatcgaagc cgccgctcaa caatcgcaga ggctgttcgg atggctgcat    540
gcgctcaatg tgatcctgat catctcttgg ccctcataca tgtcctactt caagatcttc    600
catccttcca tgtcgattac ctgcctgatg aacgccacca ttcaattcct aaagatgaca    660
tccttctcgc ttgtcaatca agacctcagg gctgcataca tctttgacct tccagaggac    720
aaattccacc atttgactcg ggtgcacgat gccaactcgg gcaacacagc aacccaacga    780
ggagaggtat accagtacga tgttcaatac cctgacaaca tcacctttat gaacgtggcc    840
tattttggt tcgcaccaac gctctgttac cagccttcgt accctcgaac gacggttttt    900
cgcaagtcgt tcttccttaa gcgcgtgggc gagatggtta cctgtgtcgg aatgatgtac    960
tttctaatcg agcagtacgc gacaccaacc ctgcaaaatt ctgttcgggc tgtgaccag   1020
ctcgcattcg ggacgatgct tgaaagagtt cttaagctga gcacaaccag tgttctcatt   1080
ggctcctca tgttctacac gttcttccat gccaccttta atgctctggg tgagcttttg   1140
tattttggcg atcgctgctt ttatctcgct tggtggaatg caggtctgt tggccgatac   1200
tgggcgctct ggaacaggcc cgtgtatgtg ttttttaaaa gacacgttta cctgccactg   1260
```

```
attagcggag gctcgtcgcc cttgacggcc atgtttgtga tctttacgat ttccgccatt    1320
ctgcacgagg tcttgattgg attcccgacg cacatgctct atggttatgc attcgcaggc    1380
atgtttgcgc agatcccgct cattgccttg acaagaccgc tcgagaagtg gcgaggtacc    1440
ggaactggac tcggcaacat gattttctgg gtatcgttca cgatcctggg ccagccggcc    1500
tgtgcgctgc tctactatta tcactggacc aagcgccata tcgatgacac gccctcgaca    1560
gtagcctga                                                            1569

<210> SEQ ID NO 3
<211> LENGTH: 27
<212> TYPE: DNA
<213> ORGANISM: Artificial sequence
<220> FEATURE:
<223> OTHER INFORMATION: synthetic DNA

<400> SEQUENCE: 3
ccggaattca tgaccaagaa cgagccc                                        27

<210> SEQ ID NO 4
<211> LENGTH: 28
<212> TYPE: DNA
<213> ORGANISM: Artificial sequence
<220> FEATURE:
<223> OTHER INFORMATION: synthetic DNA

<400> SEQUENCE: 4
ctagtctaga tcaggctact gtcgaggg                                       28

<210> SEQ ID NO 5
<211> LENGTH: 20
<212> TYPE: DNA
<213> ORGANISM: Artificial sequence
<220> FEATURE:
<223> OTHER INFORMATION: synthetic DNA

<400> SEQUENCE: 5
taatacgact cactataggg                                                20

<210> SEQ ID NO 6
<211> LENGTH: 18
<212> TYPE: DNA
<213> ORGANISM: Artificial sequence
<220> FEATURE:
<223> OTHER INFORMATION: synthetic DNA

<400> SEQUENCE: 6
tcggttagag cggatgtg                                                  18
```